United States Patent [19]

Kohayakawa et al.

[11] Patent Number: 5,237,351
[45] Date of Patent: Aug. 17, 1993

[54] VISUAL TARGET APPARATUS

[75] Inventors: Yoshimi Kohayakawa, Yokohama; Motoya Takai, Kawasaki, both of Japan

[73] Assignee: Canon Kabushiki Kaisha, Tokyo, Japan

[21] Appl. No.: 841,200

[22] Filed: Feb. 27, 1992

Related U.S. Application Data

[63] Continuation of Ser. No. 540,349, Jun. 19, 1990, abandoned.

[30] Foreign Application Priority Data

Jun. 23, 1989 [JP] Japan ................... 1-161084

[51] Int. Cl.$^5$ .............................................. A61B 3/02
[52] U.S. Cl. .................................... 351/243; 351/237
[58] Field of Search ............... 351/205, 211, 246, 243, 351/237

[56] References Cited

U.S. PATENT DOCUMENTS

| | | |
|---|---|---|
| 4,252,420 | 2/1981 | Kohayakawa . |
| 4,293,198 | 10/1981 | Kohayakawa et al. . |
| 4,697,895 | 10/1987 | Sekiguchi et al. . |
| 4,820,037 | 4/1989 | Kohayakawa et al. . |
| 4,953,968 | 9/1990 | Sherwin .............................. 351/211 |

*Primary Examiner*—Rodney B. Bovernick
*Attorney, Agent, or Firm*—Fitzpatrick, Cella, Harper & Scinto

[57] ABSTRACT

An apparatus for producing a figure as a visual image target visually recognizable by a patient to be examined, generating an image as a visual target from an image memory and displaying the visual target, and changing the size of the visual target in accordance with a change in diopter of the visual target.

22 Claims, 1 Drawing Sheet

VISUAL TARGET APPARATUS

This application is a continuation of application Ser. No. 07/540,349 filed Jun. 19, 1990, now abandoned.

BACKGROUND

1. Field of the Invention

The present invention relates to a visual target apparatus used in ophthalmic instruments such as an eye-refractometer and an optometer.

2. Related Background Art

In a visual target system in a conventional eye-refractometer, a visual target is presented by illuminating a slide film with a figure or image from behind the slide film. A facade or apparent diopter of the visual target is changed by moving an optical member. In this case, since the facade or apparent size of the visual target is not almost changed, it is therefore difficult to express a remote feeling to the visual target. More specifically, when the diopter of the visual target is gradually increased in order to guide the eye to a point at a far distance, if the size of the visual target is not sufficiently decreased, the visual target does not appear to naturally move toward a point at far distance. When such an visual target system is also employed in a eyesight test, a BADAL optical system in which the facade size of the visual target is not changed with the diopter is employed. Since the size of the visual target is not changed in this BADAL optical system, it is not suitable for inducing accommodation. Note that even if the visual target system is used in only eyesight tests, not to change the facade size of the visual target in a conventional system, a special optical system called a BADAL optical system is required.

SUMMARY OF THE INVENTION

It is a first object of the present invention to provide a visual target apparatus which can cause a patient to be examined to feel that a visual target as if located far away and which can accurately guide an eye to a point at a far distance when the visual target apparatus is used as accommodation inducing system.

It is a second object of the present invention to provide a visual target apparatus which can present the image of a visual target at a constant size when the visual target apparatus is used in an eyesight test regardless of the diopter of the patient, thereby performing accurate measurements with a simple arrangement.

It is a third object of the present invention to provide a visual target apparatus which can display an image of a mother's picture, an animation character, or a figure generated by a computer or the like which attracts infants and children, so that the visual target apparatus is suitable for dioptral and optometric measurements of infants and children.

DESCRIPTION OF THE PREFERRED EMBODIMENTS

Figure 1:
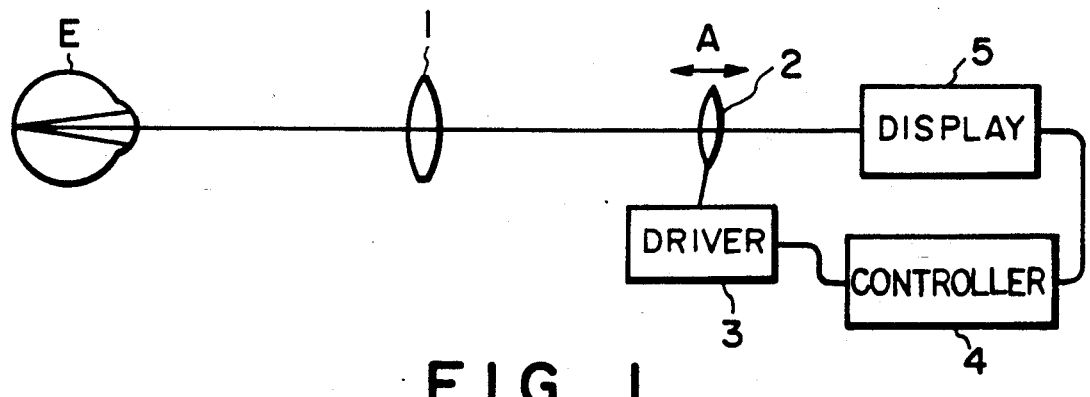
FIG. 1 is a view showing an arrangement according to the first embodiment of the present invention.

FIG. 1 shows the first embodiment of the present invention. Visual target presenting optical systems 1 and 2 are aligned on an optical axis, and the second visual target presenting optical system 2 is driven by a driver 3 in a direction indicated by an arrow A. A video display 5 such as a television monitor is arranged at a focal position of the visual target presenting optical system 2 to generate a figure or image serving as a visual target on a screen. The figure displayed on the video display 5 is synthesized by an output from a controller 4 or the image displayed on the video display 5 is generated by an image memory in accordance with an output from the controller 4.

In this case, the visual target synthesized on the video display 5 is presented to an eye E to be examined through the visual target presenting optical systems 1 and 2. The visual target presenting optical system 2 is moved by the driver 3 to match with the diopter of the eye E to be examined, thereby changing the diopter of the visual target.

Figure 2:
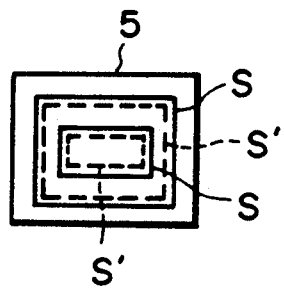
FIG. 2 is a front view showing a figure as a visual target.

FIG. 2 shows a visual target S of a figure displayed on the video display 5. When the facade diopter of the target is changed toward a far direction by the visual target presenting optical system 2 in order to guide the eye E toward a point at a far distance, a signal representing movement of the visual target presenting optical system 2 is received by the controller 4 through the driver 3. The size of the visual target S is reduced to a dotted target S' in accordance with an output from the controller 4. That is, when an object moves towards a point at a far distance in a natural state, the size of the object is reduced in inverse proportion to the distance to the object. Therefore, when the size of the visual target S is reduced based on this relationship, the patient can feel as if the visual target naturally moved toward a point at a far distance. In this case, the video display 5 itself may be moved in place of driving the visual target presenting optical system 2.

Figure 3:
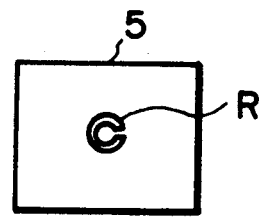
FIG. 3 is a front view showing a visual target when it is applied to an optometer according to another embodiment of the present invention.

FIG. 3 shows another embodiment in which a visual target is used in an optometer. More specifically, a Landholt ring R is presented on a video display 5. In this case, when a visual target presenting optical system 2 is moved to match with the diopter of an eye E to be examined in a direction indicated by an arrow A, a magnification is changed by the visual target presenting optical system 2 and a visual target presenting optical system 1, so that the facade size of the Landholt ring R is changed. To compensate for this, the size of the Landholt ring R is controlled by a controller 4 so as not to change the facade size of the Landholt ring R.

In the embodiment, a figure is displayed on the basis of the output from the controller 4. However, if it is needed, a VTR may be connected to display animation.

Figure 4:
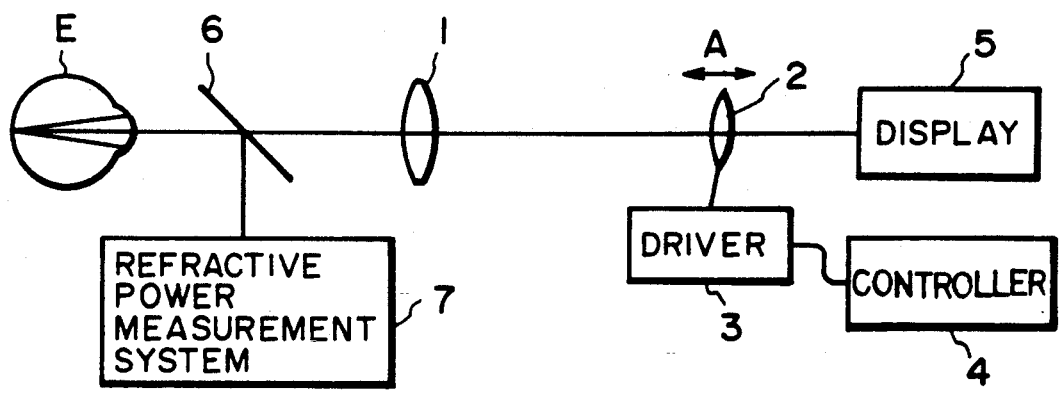
FIG. 4 is a view showing a visual target when it is applied to an eye-refractometer according to still another embodiment of the present invention.

FIG. 4 shows still another embodiment in which a visual target is applied to an eye-refractometer. Members 1 to 5 constituting the visual target apparatus are identical to those in the embodiment shown in FIG. 1. In a visual target optical path, a dichroic mirror 6 for transmitting visual light and reflecting near-infrared rays is arranged. A refractive power measurement system 7 is arranged in an optical path of light reflected by the dichroic mirror 6.

The refractive power measurement system 7 projects a visual target beam of near-infrared rays onto a fundus of an eye to be examined, causes a photosensor (e.g., a two-dimensional CCD) to receive a beam reflected by the fundus of the eye, and calculates a refractive power in accordance with an output from the photosensor.

What is claimed is:

1. A visual target apparatus comprising:
   video display means for displaying a visual target visually recognizable by a subject to be examined;
   display control means for controlling a display of said video display means; and
   an optical system for projecting the visual target image onto an eye of the object the be examined,
   wherein when at least a part of said optical system or the visual target is changed to change the optical distance from the visual target image to the eye, said display control means changes a size of the visual target in predetermined relation with the change in the optical distance from the visual target image to the eye.

2. An apparatus according to claim 1, wherein said display control means reduces the size of the visual target when the visual target optically moves to a far position.

3. An apparatus according to claim 1, further comprising an image memory, wherein the visual target is an image generated by said image memory.

4. An apparatus according to claim 1, wherein the visual target is a synthesized figure.

5. An apparatus according to claim 1, wherein the visual target is an animation image.

6. An apparatus according to claim 1, wherein the visual target is a visual target for a refractometer.

7. An apparatus according to claim 1, wherein the visual target is a visual target for an optometer.

8. An ophthalmic apparatus, comprising:
   an eye test system, opposing an eye to be examined, for detecting eye information;
   video display means for displaying a visual target to be visually recognizable by the eye; and
   an optical system for projecting the visual target image on the eye to be examined,
   wherein when at least a part of said optical system or the visual target is changed to change the optical distance from the visual target image to the eye, said display control means changes a size of the visual target in predetermined relation with the change in the optical distance from the visual target image to the eye.

9. An apparatus according to claim 8, wherein said display control means reduces the size of the visual target when the visual target optically moves to a far position.

10. An apparatus according to claim 8, further comprising an image memory, wherein the visual target is an image generated by said image memory.

11. An apparatus according to claim 8, wherein the visual target is a synthesized figure.

12. An apparatus according to claim 8, wherein the visual target is an animation image.

13. An eye-refractometer apparatus, comprising:
    measuring means for projecting a measurement visual target image on a fundus of an eye to be examined and for measuring a refractive power of the eye upon reception of light reflected by the fundus of the eye;
    video display means for displaying a visual target to be visually recognizable by the eye to be examined;
    display control means for controlling a display of said video display means; and
    an optical system for projecting the visual target image on the eye of an object to be examined,
    wherein when at least a part of said optical system or the visual target is changed to change the optical distance from the visual target image to the eye, said display control means changes a size of the visual target in predetermined relation with the change in the optical distance from the visual target image to the eye.

14. An apparatus according to claim 13, wherein said display control means reduces the size of the visual target when the visual target optically moves to a far position.

15. An apparatus according to claim 13, further comprising an image memory, wherein the visual target is an image generated by said image memory.

16. An apparatus according to claim 13, wherein the visual target is a synthesized figure.

17. An apparatus according to claim 13, wherein the visual target is an animation image.

18. An apparatus according to claim 13, wherein the visual target is a synthesized figure.

19. An apparatus according to claim 13, wherein the visual target is an animation image.

20. An apparatus according to claim 14, further comprising an image memory, wherein the visual target is an image generated by said image memory.

21. An apparatus according to claim 14, wherein the visual target is a synthesized figure.

22. An apparatus according to claim 14, wherein the visual target is an animation image.

* * * * *

UNITED STATES PATENT AND TRADEMARK OFFICE
CERTIFICATE OF CORRECTION

PATENT NO. : 5,237,351
DATED : August 17, 1993
INVENTOR(S) : YOSHIMI KOHAYAKAWA, ET AL.

It is certified that error appears in the above-indentified patent and that said Letters Patent is hereby corrected as shown below:

COLUMN 1
    Line 25, "an" should read --a--.
    Line 26, "a" should read --an--.
    Line 40, "as if" should read --is--.

COLUMN 3
    Line 11, "the object" should read --the subject--; and "the be" should read --to be--.

COLUMN 4
    Line 21, "an object" should read --a subject--.

Line 44, "20" should read --18--.
    Line 47, "21" should read --19--.
    Line 49, "22" should read --20--.

Signed and Sealed this

Twenty-seventh Day of September, 1994

Attest:

BRUCE LEHMAN

*Attesting Officer*      *Commissioner of Patents and Trademarks*